(12) United States Patent
Tominaga et al.

(10) Patent No.: US 6,448,063 B2
(45) Date of Patent: Sep. 10, 2002

(54) EXPERIMENTAL APPARATUS FOR SLICED SPECIMEN OF BIOLOGICAL TISSUE AND SPECIMEN HOLDER

(75) Inventors: Takashi Tominaga; Michinori Ichikawa, both of Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/738,266

(22) Filed: Dec. 15, 2000

(30) Foreign Application Priority Data

Dec. 17, 1999 (JP) .......................................... 11-359966

(51) Int. Cl.[7] ................................................. A01N 1/00
(52) U.S. Cl. ............................... 435/284.1; 435/288.7; 435/297.5
(58) Field of Search ........................... 435/284.1, 288.7, 435/297.1, 297.2, 297.5

(56) References Cited

U.S. PATENT DOCUMENTS 5,602,028 A  *  2/1997  Minchiunton ............... 435/401
5,627,042 A      5/1997  Hirose et al. ................ 435/8
5,811,251 A      9/1998  Hirose et al. ................ 435/8
5,958,762 A  *  9/1999  Stoppini et al. ......... 435/297.5

* cited by examiner

*Primary Examiner*—David A. Redding
(74) *Attorney, Agent, or Firm*—Rosenthal & Osha L.L.P.

(57) ABSTRACT

An experimental apparatus for performing observations of and experimental operations on a sliced specimen of a biological tissue is disclosed. The apparatus provides a high freedom for experimental operations and maintains the physiological activity of the sliced specimen. The experimental apparatus includes an experimental vessel for holding saline solution, the vessel is comparatively shallow, open at top, and transparent at least on a bottom. The apparatus also includes a specimen holder holding member for holding a specimen holder with a membrane filter at the bottom, taken out of a cultivator, a solution introduction tube for feeding fresh saline solution into the experimental vessel, and a solution discharge tube for sucking saline solution from the experimental vessel.

6 Claims, 4 Drawing Sheets

SOLUTION

TRANSMISSION
ILLUMINATION
LIGHT

EXPERIMENTAL APPARATUS FOR SLICED SPECIMEN OF BIOLOGICAL TISSUE AND SPECIMEN HOLDER

BACKGROUND OF THE INVENTION

1. Field of the Invention

The present invention relates to an experimental apparatus for a physiological experiment of a sliced specimen (slice preparation) of biological tissues while maintaining the physiological activities of the sliced specimen of the biological tissue, and a specimen holder (slice holder) to be used in the experimental apparatus.

2. Description of the Related Art

It is a basic technique of the physiological experiments to excise a part of the tissue from a biological specimen and measure its physiological activities while maintaining its physiological activities. Mostly, a sliced specimen excised from the biological tissue (simply abbreviated as a sliced specimen hereinafter), or a thin tissue piece (usually with a thickness of 1 mm or less) excised from the biological specimen is prepared:, and various physiological measurements are carried out using the specimen, because it is necessary to feed oxygen and nutrients over the entire biological tissue and remove waste products in order to maintain physiological activities of the biological tissue.

Two methods have been used for storing the sliced specimen for a long period of time while maintaining its physiological activities. The first method comprises, as shown in FIG. 5, disposing a petri dish 12 with a mesh structure for allowing a solvent to permeate in a vessel 11 filled with a saline solution 1 containing appropriate nutrients, placing a:sliced specimen 13 on the petri dish 12, and immersing and maintaining the sliced specimen 13 in the saline solution 1 while a gas mainly comprising oxygen and carbon dioxide is continuously fed into the saline solution 1 through a gas feed tube 15 equipped with a spherical filter 14.

The second method comprises, as shown in FIG. 6, placing a filter 17 (filter paper or membrane filter) that is permeable to both a solution or gas on a vessel 16 filled with the saline solution 1, mounting a sliced specimen 13 on the filter, housing the overall vessel 16 in a sealed vessel 18, and filling the inside of the sealed vessel 18 with a moist gas generated from the moisturizing saline solution 1.

The apparatuses shown in FIGS. 5 and 6 may be also used for staining the biological specimen with a biological dye. In the apparatus shown in FIG. 5, the sliced specimen 13 is stained by adding a dye in the solution 1 in which the specimen is immersed. In the apparatus shown in FIG. 6, on the other hand, the sliced specimen 13 is stained by dropping a staining solution on the specimen.

While both of the methods described above have almost the same effect for maintaining the sliced specimen 13 for a long period of time, it is a problem that the physiological activity of the sliced specimen 13 has been decreased because the sliced specimen 13 tends to be deformed and damaged when the sliced specimen 13 is transferred to a different site by taking the specimen out of the vessels 11 and 18.

While the sliced specimen 13 is transferred by sucking it with a pipette together with the solution 1 in the first method, deformation of the thin and soft sliced specimen 13 is inevitable, sometimes dealing a fatal damage to the sliced specimen 13.

While the sliced specimen 13 is peeled off from the filter 17 to transfer it into the solution in a separate vessel, the sliced specimen 13 is also liable to be imparted with a fatal damage during the transfer process. Since the sliced specimen 13 stored for a long period of time is often adhered onto the filter 17, a special care is required for peeling the sliced specimen 13 from the filter 17.

A high concentration of the dye should be maintained for a long period of time around the sliced specimen 13 in order to sufficiently and uniformly stain the biological specimen. Accordingly, the dye should be distributed in the overall solution 1 dipping the sliced specimen 13 when the apparatus shown in FIG. 5 is used for staining, which is very uneconomical because a large quantity of the usually expensive dye is needed. While consumption of the dye may be saved in the apparatus shown in FIG. 6, staining tends to be poor since it is difficult to allow a sufficient amount of the staining solution to stay around the sliced specimen 13.

Properly introducing the sliced specimen 13 into a measuring apparatus And holding the specimen there is important for measuring the physiological activities of the sliced specimen 13. The sliced specimen 13 is introduced into the measuring apparatus using a pipette together with the solution, as has been described previously. However, the physiological activities of the sliced specimen 13 may be possibly compromised by the impact of the transfer operation or by environmental changes.

It is also necessary to immerse the sliced specimen 13 in the saline solution 1, and the solution around the sliced specimen 13 should be steadily circulated in the measuring apparatus. While an appropriate weight is used for fixing the sliced specimen 13 in order to avoid the sliced specimen 13 from being displaced by the stream of the solution, the physiological activities of the sliced specimen 13 may be compromised by stress caused by the weight. The weight may also interfere the physiological measurements such as observation of transmission light and electrical potential measurements, and imaging using a dye.

The apparatus shown in FIG. 6 may be used for a cultivator by maintaining the inside of the sealed vessel 18 aseptic. However, it is difficult for the sliced specimen 13 to be transferred into the measuring apparatus without being damaged after peeling off the sliced specimen 13 from the filter 17, because the sliced specimen 13 is adhered on the filter 17. It is also impossible in general to withdraw the sliced specimen 13, subject to a aseptic treatment and resume culturing by putting it back to the cultivator after the measurement without dealing a damage to the specimen.

SUMMARY OF THE INVENTION

Accordingly, it is an object of the present invention devised for solving the technical drawbacks of the conventional art to provide an experimental apparatus for a sliced specimen of biological tissues and a specimen holder, wherein the conditions required for preservation, staining, physiological measurements and cultivation are satisfied while maintaining the sliced specimen in a condition suitable for maintaining physiological activities in each conditions above, besides subjecting the sliced specimen to an experiment by readily permitting the specimen to be transferred without being physically damaged.

A first aspect of the present invention provides an experimental apparatus for a sliced specimen of a biological tissue that is used for a physiological experiment by holding the sliced specimen of the biological tissue in a circulating saline solution while maintaining its physiological activities, comprising an experimental vessel for housing the saline solution, a specimen holder for holding the sliced specimen of the biological tissue, and a device for holding the holder for allowing the specimen holder to be attached to and detached from a prescribed position in the experimental vessel.

A second aspect of the present invention provides the specimen holder comprises an annular holder frame and a membrane filter for closing the lower part of the holder frame, the sliced specimen of the biological tissue being held on the membrane filter, in the experimental apparatus for a sliced specimen of a biological tissue of the first aspect.

A third aspect of the present invention provides holder frame has a height by ⅕ or less as small as its inner diameter, in the experimental apparatus for a sliced specimen of a biological tissue of the second aspect.

A fourth aspect of the present invention provides the membrane filter is made of a material on which the sliced specimen of the biological tissue can adheres, in the experimental apparatus for a sliced specimen of a biological tissue of the second aspect or the third aspect.

A fifth aspect of the present invention provides the membrane filter is made of a material that enhances its transparency by moisturizing, in the experimental apparatus for a sliced specimen of a biological tissue of any one of the second aspect to the fourth aspect.

A sixth aspect of the present invention provides the membrane filter has a good permeability to a gas and solution required for maintaining physiological conditions of the sliced specimen of the biological tissue, in the experimental apparatus for a sliced specimen of a biological tissue of any one of the second aspect to the fifth aspect.

A seventh aspect of the present invention provides the portion at the bottom of the experimental vessel located below the holding position of the specimen holder by the holder holding device comprises a transparent member, in the experimental apparatus for a sliced specimen of a biological tissue of any one of the first aspect to the sixth aspect.

Also, an eighth aspect of the present invention provides a specimen holder constructed so as to be able to be held by being fixed at a prescribed site in the experimental vessel by attaching to the holder holding device of the experimental apparatus for the sliced specimen of the biological tissue of the first aspect, and so as to be able to attach to and detach from the holder holding device, comprising an annular holder frame to be held by the holder holding device and a membrane filter for closing the bottom part of the holder frame, the sliced specimen of the biological tissue being held on the membrane filter.

A ninth aspect of the present invention provides the holder frame has a height by ⅕ or less as small as its inner diameter in the specimen holder in the eighth aspect.

A tenth aspect of the present invention provides the membrane filter is made of a material on which the sliced specimen of the biological tissue can adheres in the specimen holder of the eighth aspect or the ninth aspect.

An eleventh aspect of the present invention provides a material that enhances its transparency by moisturizing is used for the material for the membrane filter in the specimen holder of any one of the eighth aspect to the tenth aspect.

A twelfth aspect of the present invention provides the membrane filter has a good permeability to a gas and solution required for maintaining physiological conditions of the sliced specimen of the biological tissue in the specimen holder of any one of the eighth aspect to the eleventh aspect.

The first aspect of the present invention so configured as described above enables an experiment comprising the steps of introducing the sliced specimen of the biological tissue with the specimen holder into the experimental vessel in which the saline solution is circulating, readily disposing the sliced specimen of the biological tissue at a prescribed site in the experimental vessel by attaching the specimen holder to the holder holding device, and readily taking the sliced specimen of the biological tissue out of the experimental vessel together with the specimen holder by detaching the specimen holder from the holder holding device after completing the experiment. Since the sliced specimen of the biological tissue is transferred together with the specimen holder, the sliced specimen of the biological tissue can be readily transferred without dealing a physical damage to the specimen. Consequently, the sliced specimen of the biological tissue can be withdrawn together with the specimen holder after completing the experiment, and subjected to an septic treatment to resume cultivation by returning the intact specimen to the cultivator.

According to the second aspect and the eighth aspect of the present invention, the sliced specimen of the biological tissue is held while maintaining its physiological activities besides permitting the sliced specimen of the biological tissue to be readily transferred without dealing a physical damage to the specimen, using a specimen holder having a simple structure comprising: an annular holder frame and a membrane filter for closing the lower part of the frame folder. Since good staining of the sliced specimen of the biological tissue is possible using a small quantity of a staining solution by allowing an amount of the staining solution sufficient for staining the sliced specimen to pool around the sliced specimen by injecting the staining solution to the inside of the holder frame of the specimen holder holding the sliced specimen of the biological tissue, the expense of the experiment can be saved by largely reducing consumption of the staining solution.

According to the third aspect and the ninth aspect of the present invention, the experimental work such as attaching electrodes to the sliced specimen of the biological tissue while holding the sliced specimen of the biological tissue with the specimen holder is made easy since the holder frame of the specimen holder has a height by ⅕ as small as the inner diameter of the holder.

According to the fourth aspect and the tenth aspect of the present invention, displacement of the sliced. specimen of the biological tissue when the sliced specimen of the biological tissue is transferred together with the specimen holder or the solution around the specimen is exchanged, and by circulation of the solution in the experimental vessel, can be prevented, since the sliced specimen of the biological tissue is adhered to and integrated with the membrane filter on the specimen holder. Accordingly, a weight for pressing the sliced specimen of the biological tissue is not needed because the sliced specimen of the biological tissue is not displaced by the flow of the solution during the experiment. Consequently, drawbacks that the physiological activities of the sliced specimen of the biological tissue are compromised by being pressed with the weight can be solved, besides eliminating interference of the weight for physiological measurements such as observation of transmission light, measurement of electrical potential and imaging using a dye.

According to the fifth aspect and the eleventh aspect of the present invention, experiments and observation of the sliced specimen of the biological tissue are possible while mounting the specimen on the specimen holder, because the membrane filter turns out to be more transparent when the specimen holder is dipped in the saline solution.

According to the sixth aspect and the twelfth aspect of the present invention, physiological state of the sliced specimen of the biological tissue can be maintained in good conditions during the experiments.

According to the seventh aspect of the present invention, observation by a transmission light is possible by attaching the specimen holder holding the sliced specimen of the biological tissue to the holder holding device and by illuminating the specimen with an illumination light from below the experimental vessel, since good physiological conditions of the sliced specimen of the biological tissue are maintained by circulating the saline solution in the experimental vessel.

DESCRIPTION OF THE PREFERRED EMBODIMENTS

The present invention will be described in detail based on the embodiments.

Figure 1A:
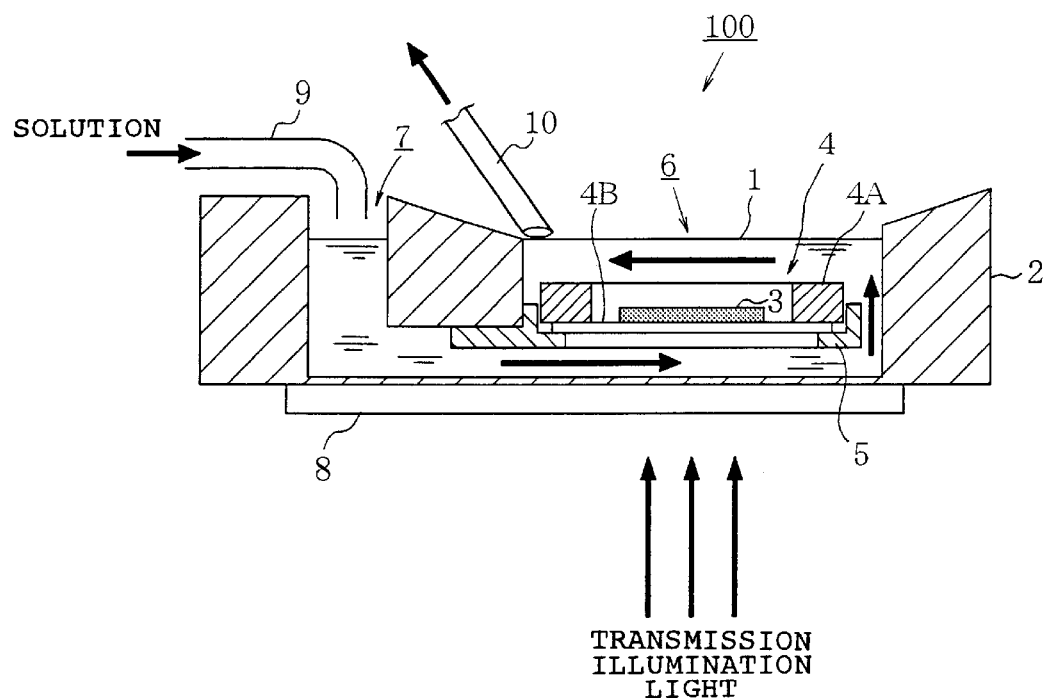
FIG. 1A is a vertical cross section showing one example of the structure of the experimental apparatus for the sliced specimen 6f the biological tissue according to the present invention.
Figure 1B:
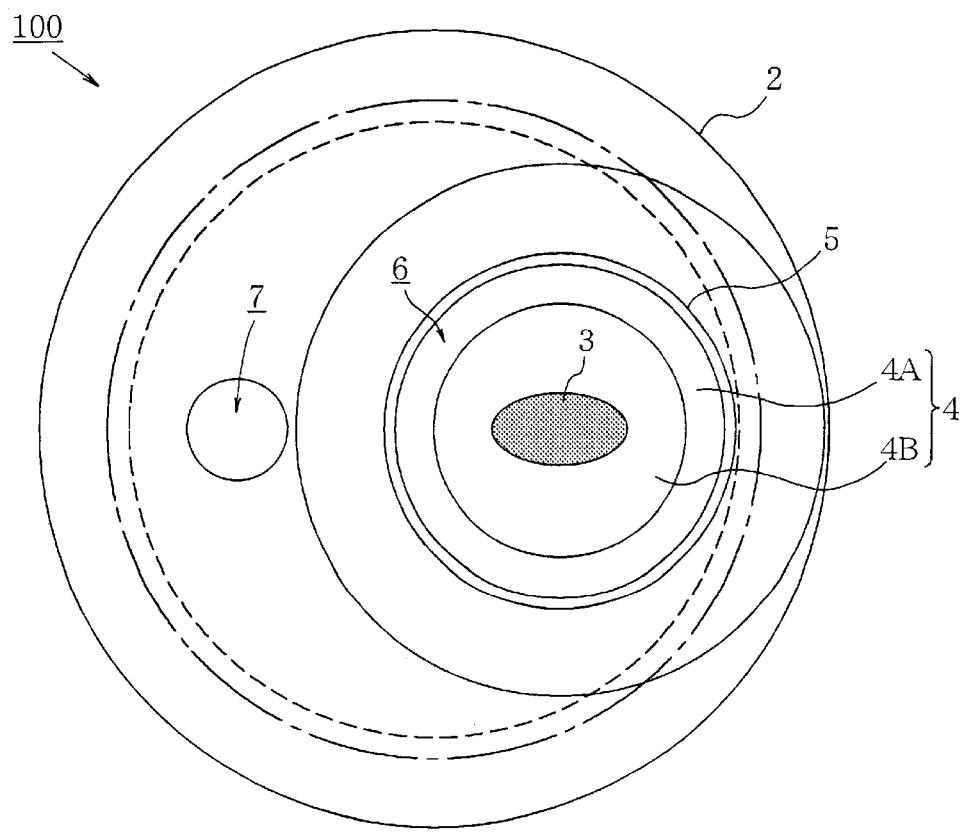
FIG. 1B is a plane view showing one example of the structure of an experimental apparatus for the sliced specimen of the biological tissue according to the present invention.

FIGS. 1A and 1B show one embodiment of the present invention. FIGS. 1A and 1B are a vertical cross section and plane view showing the structure of the experimental apparatus for the sliced specimen of the biological tissue, respectively.

The experimental apparatus 100 comprises an experimental vessel 2 for housing a saline solution 1, a specimen holder 4 for holding a spliced specimen 3, and a holder holding member (holder holding device) 5 for holding the specimen holder 4 at a prescribed site in the experimental vessel 2.

A holder attachment port 6 for inserting and releasing the specimen holder 4 and a solution inlet port 7 for introducing the saline solution 1 is provided at the upper part of the experimental vessel 2. The bottom of the experimental vessel 2 comprises a transparent glass plate 8.

A solution introduction tube 9 is inserted into the solution inlet port 7, and a solution discharge tube 10 is inserted into the holder attachment port 6. The solution introduction tube 9 and the solution discharge tube 10 are connected to a solution circulation device (not shown), and the liquid level in the experimental vessel 2 is always kept constant by discharging the saline solution 1 circulating in the experimental vessel 2 through the solution discharge tube 10, while feeding a fresh saline solution 1 in the experimental vessel 2 through the solution introduction tube 9. The saline solution 1 is at first led from the solution inlet port 7 to the bottom of the vessel, ascends through the gap between the bottom face of the vessel (upper face of a glass plate 8) and the specimen holder 4, and is finally sucked out through the solution discharge tube 10 after flowing on the specimen holder 4. A proper exchange of the solution and gas around the sliced specimen 3, which is one of the crucial conditions in the physiological experiment, can be realized by circulating the solution.

The experimental apparatus 100 may be also available for used as a so-called liquid-gas phase experimental vessel ("interface"-type chamber), when the liquid level in the experimental vessel 2 is descended to be lower than the surface of the sliced specimen 3, and a moist gas is fed to the sliced specimen 3 through a gas feed tube (not shown).

Figure 2A:
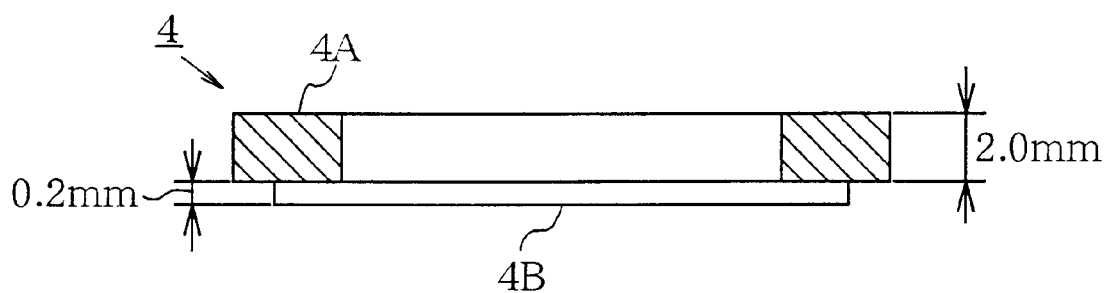
FIG. 2A is a vertical cross section showing one example of the structure of the specimen holder according to the present invention.
Figure 2B:
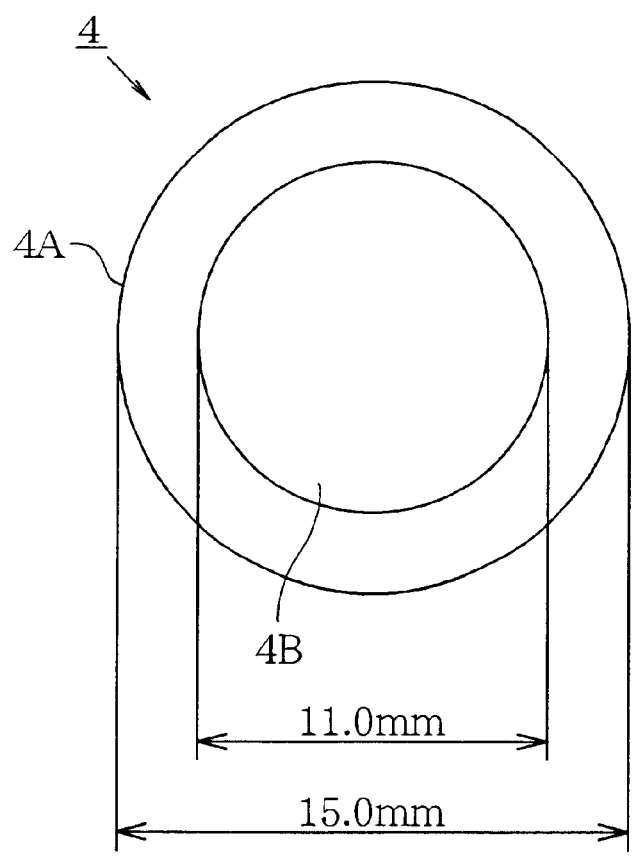
FIG. 2B is a plane view showing one example of the structure of the specimen holder according to the present invention.

A membrane filter 4B having a good permeability to the gas and saline solution 1 required for maintaining a good physiological state of the sliced specimen 3 is adhered on the lower face of a thin and annular holder frame 4A in the specimen holder 4 as shown in FIGS. 2A and 2B, thereby enabling the sliced specimen 3 to be held on the membrane filter 4B. The height of the holder frame 4A of the specimen holder 4 is designed to be by $\frac{1}{5}$ as small as the inner diameter of the holder frame. The dimension of each part of the practically manufactured specimen holder is shown in FIGS. 2A and 2B as a reference.

Acrylic resins and plastics are used for the holder frame 4A. PTFE (poly-tetrafluoroethylene) is used for the membrane filter 4B. Transparency of the membrane filter made of PTFE is enhanced to be almost completely transparent by absorbing water. The sliced specimen can readily adhere to the membrane filter made of PTFE, particularly during cultivation.

Figure 3A:
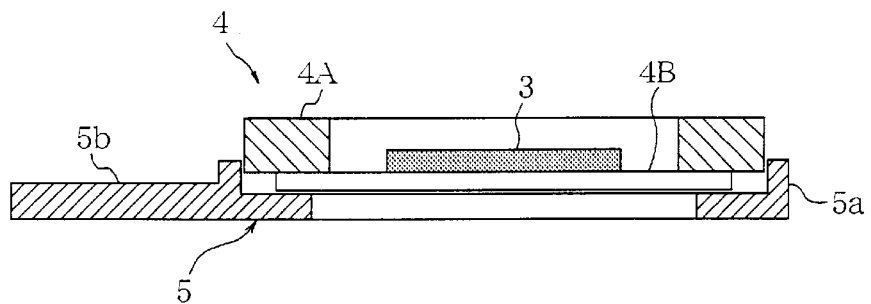
FIG. 3A is a vertical cross section showing one example of the specimen holder held by the holder holding member.
Figure 3B:
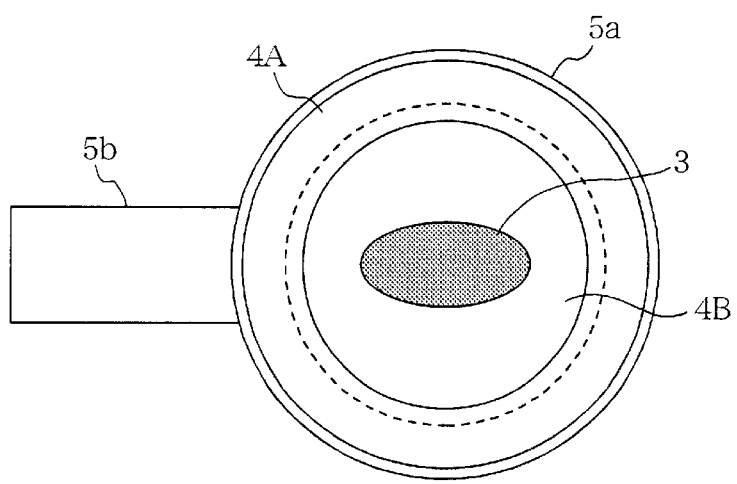
FIG. 3B is a plane view showing one example of the specimen holder held by the holder holding member.
Figure 4A:
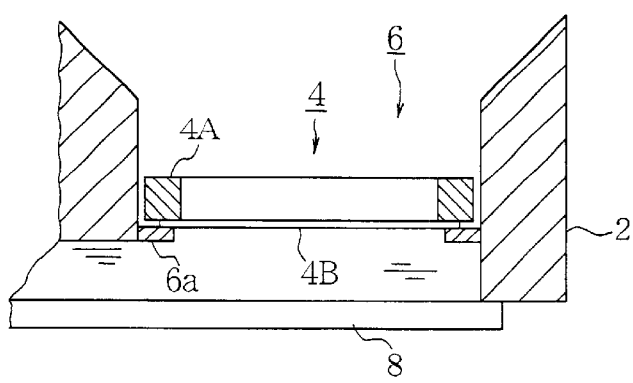
FIG. 4A is a partial vertical cross section of an another embodiment of the holder attachment port.
Figure 4B:
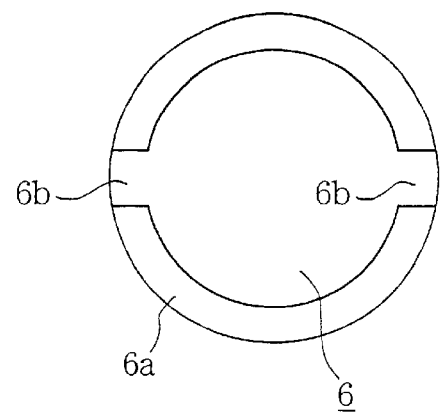
FIG. 4B is a plane view of an another embodiment of the holder attachment port.
Figure 5:
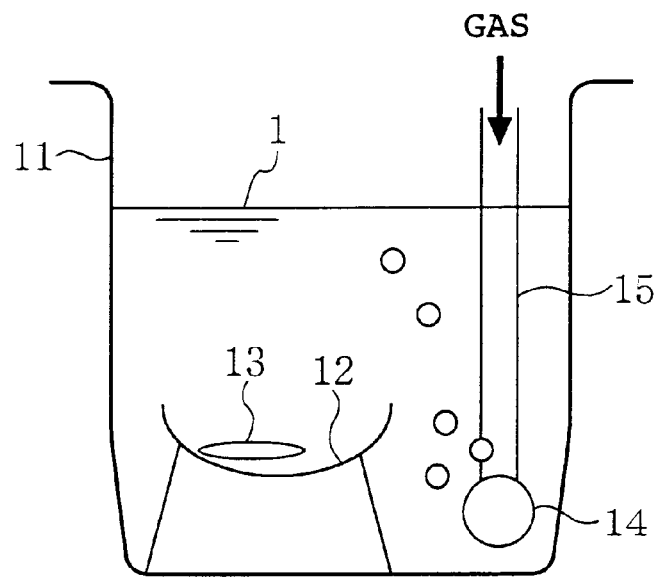
FIG. 5 illustrates a conventional experimental apparatus for the sliced specimen of the biological tissue.

As shown in FIGS. 3A and 3B, the holder holding member 5 comprises a holding part 5a that fits to the holder frame 4A of the sample holder 4 and the peripheral edge of the membrane filter 4B, and a fixing member 5b to be fixed to the vessel body of the experimental vessel 2. The sample holder 4 is horizontally held at an intermediate elevation along the vertical direction in the experimental vessel 2 by the holder holding member 5.

According to the experimental apparatus 100 of this embodiment so configured as described above, the sliced specimen 3 can be easily placed at a prescribed position in the experimental vessel 2 by introducing the sliced specimen 3 with the specimen holder 4 into the experimental vessel 2 in which the saline solution 1 is circulating, and attaching the specimen holder 4 on the holder holding member 5 in each experiment. The sliced specimen 3 can be also readily taken out of the experimental vessel 2 together with the specimen holder 4 by removing the specimen holder 4 from the holder holding member 5 after completing the experiment. Since the sliced specimen 3 is transferred together with the specimen holder 4, the sliced specimen 3 can be readily transferred without dealing a physical damage to the specimen.

The membrane filter 4B turns out to be transparent by dipping the specimen holder 4 into the saline solution 1, and the bottom of the experimental vessel 2 comprises the glass plate 8. The specimen holder 4 holding the sliced specimen 3 is attached to the holder holding member 5, and a transmission light is irradiated from below the experimental vessel 2. Accordingly, experimental works such as observation of the specimen under a transmission light and piercing of electrodes by observing the sliced specimen 3 under the transmission light can be carried out while maintaining good physiological activities of the sliced specimen 3 with the saline solution 1 circulating in the experimental vessel 2.

Figure 6:
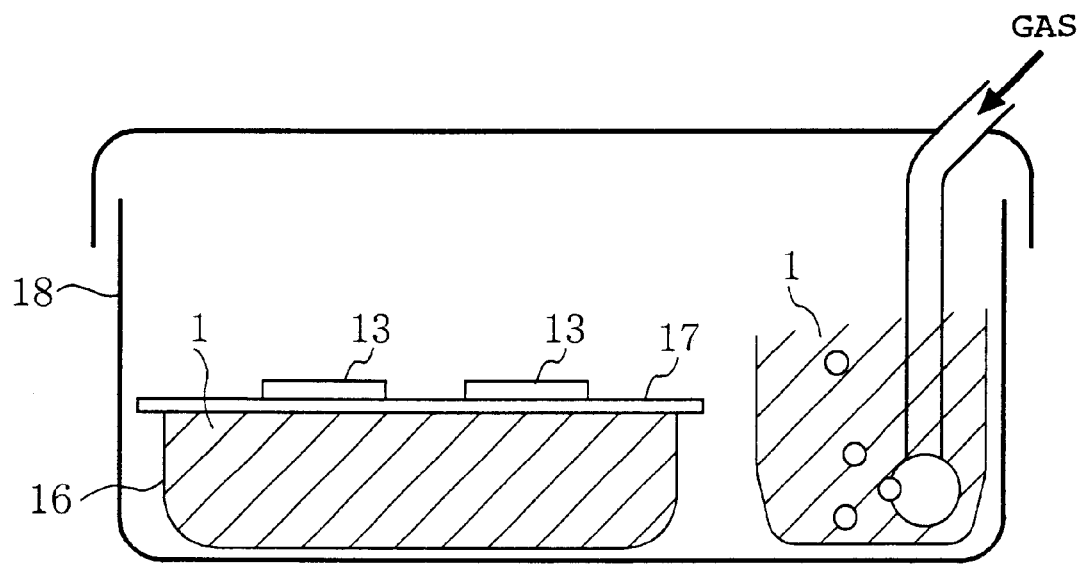
FIG. 6 illustrates an another conventional experimental apparatus for the sliced specimen of the biological tissue.

The sliced specimen 3 can be preserved in a preservation device for a long period of time while the specimen is held by the specimen holder 4, and can be transferred into the experimental apparatus 100 when required. When the apparatus shown in FIG. 6 is used, for example, the sliced specimen 3 can be preserved for a long period of time by mounting the specimen holder 4 holding the sliced specimen 3 on the filter 17, and by filling the inside of the sealed vessel 18 with a gas enriched with oxygen.

The sliced specimen 3 is withdrawn together with the specimen holder 4 after completing the experiment. After sterilization by washing the specimen with a solution containing an antibiotic, the sliced specimen 3 including the specimen holder 4 is placed in an incubator using a culture medium containing trace nutrients in place of the saline solution 1 and adequately controlling the temperature, thereby enabling cultivation to be resumed.

A staining solution (such as a solution of a membrane potential sensitive dye, a solution of calcium indicator dye and a small molecular weight staining dye solution for intracellular signal transfer) may be injected into the inside of the holder frame 4A of the specimen holder 4 holding the sliced specimen 3. Consequently, the expense of the experiment may be saved by largely reducing consumption of the staining solution, because good staining is possible by allowing a volume of the staining solution sufficient for staining to pool around the sliced specimen 3 using a small total volume of the staining solution. The expense of reagents may be also saved by largely reducing consumption of them, because the specimen can be pretreated by the same method as staining.

Since the height of the holder frame 4A of the specimen holder 4 is by $\frac{1}{5}$ as low as the inner diameter of the frame, electrodes may be inserted into the sliced specimen 3 while allowing the specimen holder 4 to hold the sliced specimen 3.

The sliced specimen 3 adheres to the membrane filter 4B and is hardly displaced when the sliced specimen 3 is mounted on the membrane filter 4B for a while. Accordingly, displacement of the sliced specimen 3 caused by transfer of the sliced specimen 3 together with the specimen holder 4, by exchange of the solution 1 around the specimen, and by circulation of the solution 1 in the experimental vessel 2 may be prevented. No weight is required for pressing the sliced specimen 3, because the sliced specimen 3 never displaces by the flow of the solution 1 during the experiment. Consequently, drawbacks such as compromising physiological activities of the sliced specimen 3 due to compression of the weight may be solved, or interference of the weight in physiological measurements such as imaging using a dye may be eliminated.

While an annular holder frame 4A of the specimen holder 4 has been used in the embodiment described above, the shape of the frame is not restricted thereto, but a holder frame with a rectangular or ellipsoidal shape may be used. The holder frame 4A is not necessarily made of an acrylic resin or plastic, but any material may be used so long as it does not adversely affect the sliced specimen 3, and has an appropriate strength. The membrane filter 4B is not necessarily made of PTFE, but any material may be used;so long as it has a high permeability to the gas necessary for maintaining physiological conditions of the sliced specimen 3, its transparency is improved by moisturizing it, and the sliced specimen 3 is ready to adhere on it.

The holder is held on holder holding member according to the claims of the present invention by forming the holder holding member 5 as a separate part from the experimental vessel 2, and by fixing the holder holding member at below the holder attachment port 6. However, it is needless to say that the holder holding member 5 may be formed by integrating it with the experimental vessel 2. For example, a projection 6a for engaging with the specimen holder 4 is formed to integrate with the inner circumference of the lower end of the holder attachment port 6. The specimen holder 4 is horizontally held by being engaged with the projection 6a when the specimen holder 4 is attached to the holder attachment port 6, thereby allowing the experimental vessel 2 itself to serve as a holder holding device. It is desirable that chipped portions 6b are formed here and there so that the projection 6a does not interfere circulation of the solution.

While the entire bottom of the experimental vessel 2 comprises the transparent glass plate 8, at least the portion located at below the specimen holder 4 on the bottom of the experimental vessel 2 may comprise a transparent member.

As hitherto described, the present invention exerts excellent effects as will be described below.

According to the first aspect of the present invention, the sliced specimen of the biological tissue with the specimen holder can be readily placed at a prescribed site in the experimental vessel by introducing the sliced specimen of the biological tissue into the experimental vessel in which the saline solution is circulating, and by attaching the specimen holder to the holder holding device during the experiment. The sliced specimen of the biological tissue can be readily taken out of the experimental vessel together with the specimen holder by removing the specimen holder from the holder holding device after completing the experiment. Also, the sliced specimen of the biological tissue can be withdrawn together with the specimen holder after completing the experiment to subject it to a sterilization treatment, enabling cultivation to be resumed by returning the intact specimen to the cultivator.

Handling of the sliced specimen of the biological tissue in the experiment is made easier as compared with the conventional experiments, since the sliced specimen of the biological tissue suffers physical stress only in preparation of the specimen by allowing the sliced specimen of the biological tissue to be held on the specimen holder, and by allowing the specimen to transfer together with the specimen holder. Accordingly, the present invention can contribute to many investigations not only in the physiological studies, but also in the investigations for studying fine textures of biological materials, and in the field of histochemical studies.

Also, according to the second aspect and the eighth aspect of the present invention, the sliced specimen of the biological tissue may be preserved while maintaining its physiological activities besides permitting the sliced specimen of the biological tissue to be readily transferred without dealing a physical damage to the specimen, by using a specimen holder with a simple structure comprising an annular holder frame and a membrane filter for closing the lower part of the holder frame. The expense of the experiment may be saved by largely reducing consumption of the staining solution, because good staining is possible by allowing a volume of the staining solution sufficient for staining to pool for a long period of time around the sliced specimen using a small total volume of the staining solution, by injecting the staining solution into the inside of the holder frame of the specimen holder holding the sliced specimen of the biological tissue.

Also, according to the third aspect and the ninth aspect of the present invention, since the height of the holder frame of the specimen holder is by 1/5 as low as the inner diameter of the frame, experimental works such as inserting electrodes into the sliced specimen of the biological tissue is made easy while allowing the specimen holder to hold the sliced specimen of the biological tissue.

Also, according to the fourth aspect and the tenth aspect of the present invention, displacement of the sliced specimen of the biological tissue when the sliced specimen of the biological tissue is transferred together with the specimen holder or the solution around the specimen is exchanged, and by circulation of the solution in the experimental vessel, can be prevented, since the sliced specimen of the biological tissue is adhered to and integrated with the membrane filter on the specimen holder. Accordingly, a weight for pressing the sliced specimen of the biological tissue is not needed because the sliced specimen of the biological tissue is not displaced by the flow of the solution during the experiment. Consequently, drawbacks that the biological activities of the sliced specimen of the biological tissue are compromised by being pressed with the weight can be solved, besides eliminating interference of the weight for physiological measurements such as observation of transmission light, measurement of electrical potential and imaging using a dye.

Also, according to the fifth aspect and the eleventh aspect of the present invention, since transparency of the membrane filter is enhanced by dipping the specimen holder into the saline solution, the specimen may be observed with the transmission light while the sliced specimen of the biological tissue is held on the specimen holder.

Also, according to the sixth aspect and the twelfth aspect of the present invention, physiological conditions of the sliced specimen of the biological tissue may be maintained in good conditions.

Also, according to the seventh aspect of the present invention, an observation with a transmission light may be possible while maintaining good physiological activities of the sliced specimen of the biological tissue with the saline solution circulating in the experimental vessel, by attaching the specimen holder holding the sliced specimen of the biological tissue to the holder holding device, and by irradiating an illumination light from below the experimental vessel.

What is claimed is:

1. An experimental apparatus for a sliced specimen of a biological tissue used for performing physiological experiments holding a sliced specimen in a circulated saline solution and thereby maintaining physiological activities of the sliced specimen, comprising:

an experimental vessel for holding saline solution;

a specimen holder for holding the sliced specimen of the biological tissue, the specimen holder comprising a ring-shaped holder frame with a top and a bottom opening and a membrane filter closing the bottom opening of the holder frame when taken out of a cultivator and put in the experimental vessel;

a specimen holder holding member for detachably holding the specimen holder in an interior space of the experimental vessel;

a solution introduction tube for feeding fresh saline solution into the experimental vessel; and a solution discharge tube for sucking the saline solution from the experimental vessel;

wherein the experimental vessel is comparatively shallow and open at a top portion thereof, wherein at least a part of a. bottom of the experimental vessel under the specimen holder mounted on the specimen holder holding member is transparent, wherein the specimen holder is held by the specimen holder holding member in the experimental vessel such that a desired spacing exits between the membrane filter and the bottom of the experimental vessel, and wherein the liquid level in the experimental vessel is adjusted by a height of the solution discharge tube, and the liquid level is kept constant at the height.

2. The experimental apparatus for a sliced specimen of a biological tissue according to claim 1, further comprising a member enclosing the specimen holder mounted on the specimen holder holding member and protruding above a liquid surface and having a passage for the liquid connecting a space above the specimen holder with a space below the specimen holder formed between the specimen holder and the specimen holder holding member and the member enclosing the specimen holder, and wherein the solution introduction tube is disposed so as to feed the saline solution into the experimental vessel outside the space enclosed by the member enclosing the specimen holder, and the solution discharge tube is disposed so as to suck the saline solution inside the space enclosed by the member enclosing the specimen holder.

3. The experimental apparatus according to claim 1, wherein the membrane filter is made of a material to which the sliced specimen of a biological tissue can readily stick and which becomes highly transparent when soaked with water.

4. The experimental apparatus according to claim 3, wherein a height of the holder frame is equal to or smaller than one fifth of the internal diameter of the holder frame.

5. The experimental apparatus according to claim 2, wherein the membrane filter is made of a material to which the sliced specimen of a biological tissue can readily stick and which becomes highly transparent when soaked with water.

6. The experimental apparatus according to claim 5, wherein a height of the holder frame is equal to or smaller than one of an internal diameter of the holder frame.

* * * * *